United States Patent [19]
Martinez

[11] Patent Number: 5,756,100
[45] Date of Patent: May 26, 1998

[54] METHOD AND MATERIAL FOR REPELLING PESTS FROM AGRICULTURAL CROPS

[76] Inventor: Leo Martinez, Rte. 1, Box 312, Delano, Calif. 93215

[21] Appl. No.: 802,441

[22] Filed: Feb. 18, 1997

[51] Int. Cl.$^6$ .......................... A01M 65/00; A01M 59/00; A01M 59/02
[52] U.S. Cl. ...................... 424/195.1; 424/600; 424/693; 424/DIG. 10
[58] Field of Search .................. 424/195.1, DIG. 10, 424/693, 600

[56] References Cited

U.S. PATENT DOCUMENTS

| | | | |
|---|---|---|---|
| 5,344,649 | 9/1994 | Mungia | 424/195.1 |
| 5,466,459 | 11/1995 | Wilson | 424/407 |
| 5,525,576 | 6/1996 | Medina-Vga et al. | 504/116 |
| 5,525,597 | 6/1996 | Hainrihar et al. | 514/627 |

*Primary Examiner*—Herbert J. Lilling
*Attorney, Agent, or Firm*—Dennis B. Haase

[57] ABSTRACT

A repellent for agricultural crops that uses accepted all natural components to protect crops organically. The repellent uses a combination of red pepper, powdered, garlic and black pepper to repel undesirable pests. Hydrated calcium hydroxide is added to the combination to increase the stability of the resultant mixture. The calcium hydroxide also acts as a fertilizer on some soils by increasing soil pH. The peppers contain alkaloids that yield nitrogen when decomposed fully. The repellent comprises, by weight percentage, between 3% and 20% red pepper, between 3% and 20% powdered garlic, between 3% and 20% black pepper, and between 40% and 91% hydrated calcium hydroxide. Preferably, the repellent comprises 10.7% red pepper, 10.7% powdered garlic, 10.6 black pepper and 68% hydrated calcium hydroxide. The repellent components are combined and thoroughly blended to produce a mixture that may be applied to any crop to prevent most pest infestations. The mixture may be applied with known conventional applicators, including aerial crop dusters. The mixture does not harm plants and/or people and/or livestock at practical application rates. Therefore, potential damage to adjacent crops and/or areas is minimized when aerially applying the mixture.

12 Claims, No Drawings

5,756,100

METHOD AND MATERIAL FOR REPELLING PESTS FROM AGRICULTURAL CROPS

The present invention generally relates to a repellent suitable for use on agricultural crops to protect the crop from undesirable pests. More specifically, the invention relates to a dry particulate, nontoxic repellent with a fertilizing primary component that may be applied onto organically grown crops. Prior art may be found in U.S. Class 424 and the various subclasses thereunder.

BACKGROUND OF THE INVENTION

FIELD OF THE INVENTION

It is well known in the agricultural arts, and particularly to the farmer, that over the years a genetic battle has raged between the scientist, whose efforts are dedicated to the eradication of agricultural pests, and the pests themselves. Since the prohibition of the use of DDT, various strains of vectors such as flies, locusts, aphids, weevils, etc. have seemingly mutated so as to build resistance to various chemicals that scientists have developed to control them. Yet, the quality, and in some cases the very existence of a crop, is dependent on the ability of the farmer to control agricultural pests, a task made even more difficult in recent times by the limitations and licenses placed on a large variety of chemicals by the EPA, both state and federal. Simply stated, the farmer must find a suitable way to control crops, or see his or her efforts go for naught. The farmer has a couple of options. He or she may either eradicate, or repulse the pests to control or prevent destructive infestations. In general, pesticides eradicate undesirable pests, while repellents repulse them. In the recent past, pesticides that utilize synthetic chemicals have been the principal vehicle upon which many farmers have relied. The consuming public, on the other hand, has become increasingly cautious about what they consume, and large and powerful environmental groups have successfully inhibited, in many cases, the use of several otherwise very effective chemicals, to the farmer's detriment.

Coincidently, the recent tightening of both Federal and State environmental and pollution control laws and regulations have made chemical eradication more difficult and costly. For example, the State of California alone has promulgated a list of over 350 chemicals deemed to be toxic. Such chemicals have meticulous rules and regulations governing their availability and use and, in many instances, require licenses for their application and use. As can well be imagined, California farmers in particular, and farmers nationwide generally, are severely handicapped by such rules and regulations and are constantly seeking alternatives to time honored eradication procedures.

Increasing consumer awareness of potential hazards associated with synthetic chemical usage, coupled with an explosion of lawsuits by farm workers for exposure, has created and promoted a farming method, once a cottage industry, until demand for produce often referred to as "all natural" or "organic" has become big business.

For example, apples and grapes have both been the subject of disconcerting public revelations detailing purported hazards of chemicals commonly used during their production. The Alar scare in the Northwest is but one of several examples in which the public's perception almost crippled an entire industry. As a result, organically grown produce has become increasingly attractive and profitable for the enterprising farmer.

Since organic produce typically must be grown without the aid of products that contain synthetic chemicals in order to obtain certification, such organically grown produce is susceptible to depredation by predatory pests unless acceptable control methods are developed and implemented by the farmer.

OVERVIEW OF THE PRIOR ART

As a consequence of the increasing development, certification, and production costs for pesticides and the increased demand for organic produce, efforts to find suitable alternatives to pesticides that contain synthetic chemical eradicators have been accelerated. At least one such alternative includes the use of repellents in lieu of pesticides.

It remains common practice for farmers to simply exterminate undesirable pests with chemical pesticides after they infested a field. Unfortunately, most of the chemical pesticides in current use also indiscriminately kill beneficial insects that provide a measure of natural predatory control. Furthermore, most known pesticides generally have little residual activity. In other words, they do not keep killing pests in the field for any appreciable period after the initial application.

As a result, frequent reapplications are normally required to maintain adequate control. On the other hand, repellents typically prevent infestations, and they may continue repulsing pests for considerable periods of time when left undisturbed.

Since several naturally occurring substances are known to more or less effectively repel many pests, repellents are an attractive alternative. For example, Messina U.S. Pat. No. 4,965,070, Loucas U.S. Pat. No. 5,368,866, Plummer et al. U.S. Pat. No. 5,240,708 and McKenzie U.S. Pat. No. 5,429, 817 all discuss various liquid compositions that repel, as distinguished from eradicating, pests. Messina, Loucas and Plummer use a pepper repellent, while the McKenzie patent utilizes garlic. All four require an adhesive to insure that the repellent will adhere to the proper part of the protected plants after being applied.

A repellent for protecting inaccessible areas in house and barns from rodents is discussed in Harding, Jr. U.S. Pat. No. 4,795,637. The repellent comprises a mixture of thujone oil with at least one atomizing resistant powder. The powders discussed generally have densities between 0.9 g/cc and 1.0 g/cc. While the mentioned powders include pepper, thujone oil is identified as the repelling component. Unfortunately, thujone oil does not repel all pests. Moreover, it is not believed that thujone oil is an acceptable compound for organic certified produce. Thus, farmers desiring to advertise and sell their crop as certified organic produce may find that this powder will not qualify.

A proposed liquid organic pesticide is detailed in Wilson U.S. Pat. No. 5,466,459. This pesticide combines concentrated capsaicin, derived from peppers, with refined wax and other scents to, primarily, eradicate mites when applied in an aqueous solution to plants. The wax coats the protected plan to suffocate mites, while the capsaicin stimulates their central nervous system. The patent briefly discusses an optional water soluble fertilizer packet, principally composed of kelp, that may also be included in the aqueous solution.

However, several problems may be experienced with liquid pesticides and/or repellents. First, large amounts of water are often required to suspend the pesticide and/or repellent in an aqueous solution. Thus, the quantity of material that must be transported over the crop is increased correspondingly. The increase in material quantity to be dispersed necessarily increases the number of trips the applicator must make over the crop. There is an inherent increased likelihood of crop damage, or equipment failure, or both.

Also, liquids typically cover only that portion of the plant facing the path of the material being applied. Pests which adhere to the underside of leaves, or protected fruit, may not be exposed. Thus, such limited coverage results in decreased efficiency at a crucial period of crop production.

Limited coverage is even a more likely consequence and, thus, problematic when the liquids are applied aerially, and aerially applied liquids are susceptible to wind caused drift and evaporation. Since many farms are quite large, often exceeding 100 acres, aerial application or crop dusting is a preferential method of applying materials quickly. The inherent danger of crop dusting involves drift onto adjacent crops and/or inhabited locations. Many prior pesticides could harm the adjacent crops, or the like, if they drifted thereon. Solid materials that resist drift are, consequently, preferable for aerial application.

Thus, there is a continuing need for an acceptable repellent that may be effectively used with agricultural crops, particularly edible crops that go directly from the field to the market (i.e., grapes, citrus, nuts, tomatoes, etc.).

A desirable repellent should avoid synthetic chemicals so that the farmer could grow crops organically. An even more desirable repellent would permit aerial application on selected crops, while avoiding uncontrolled drift upon adjacent crops. Such a repellent should also minimize potential crop damage if unforeseen drift unintentionally occurred during aerial application.

In some areas, an ideal repellent should comprise ingredients that also function as fertilizers as they decompose. Thus, an ideal repellent would comprise components that would function as fertilizers when they decompose.

SUMMARY OF THE INVENTION

The within described repellent for agricultural crops overcomes the problems with the prior art, both perceived and real. The repellent may also be aerially applied with minimal undesirable drift and negligible damage to neighboring crops. When aerially applied, the repellent, by virtue of its particulate state, still effectively protects lower plant portions.

The repellent, in its preferred form, uses a combination of red pepper, powdered garlic and black pepper to repel undesirable pests. Hydrated calcium hydroxide is added to the combination to increase the stability of the resultant mixture. It has also been determined that the judicious use of fine ground sulphur is beneficial, in combination with the calcium hydroxide, as will be pointed out hereinafter.

The calcium hydroxide also acts as a fertilizer on some soils by increasing soil pH. Of course, the peppers contain alkaloids (primarily cyclic nitrogen compounds) that yield nitrogen when fully decomposed. Thus, the ingredients of the repellent have the capacity to nourish the plant as they decompose.

The repellent, in its most effective form, comprises, percentages representing ranges by weight, between 10.7% and 20% red pepper, between 10.7% and 20% powdered garlic, between 10.6% and 20% black pepper, and between 40% and 68% hydrated calcium hydroxide. Preferably, the repellent comprises 10.7% red pepper, 10.7% powdered garlic, 10.6% black pepper and 68% hydrated calcium hydroxide. The repellent, in components, is particulate in form, and combined and thoroughly blended to produce an essentially homogenius admixture that may be applied to any crop to prevent most pest infestations. It will be appreciated that the discovery described herein was initially developed for grapes in the San Jauquin valley.

The mixture may be applied with known conventional applicators (i.e., over the top dusters, crop dusters, etc.). Of particular interest, the mixture may be advantageously applied aerially. Furthermore, the mixture itself does not harm plants and/or people and/or livestock at practical application rates. Therefore, potential damage to adjacent crops and/or areas is minimized when aerially applying the mixture.

Thus, a primary object of the present invention is to provide a repellent that may be used on crops to protect them from pests.

A related object of the present invention is to provide a repellent made from natural components that may be used on organically grown crops.

A basic object of the present invention is to provide a repellent that may be aerially applied.

A related object is to provide a repellent that resists drift during aerial application.

Yet another related object is to provide a repellent that minimizes damage caused by unintentional drift.

Another object of the present invention is to provide a repellent that may be applied to the same crop several times during a single growing season without damaging or staining the corp. It is a feature of the invention that it also raises the soil pH, thus, functioning as a fertilizer.

A more basic object of the present invention is to provide a repellent that completely covers a crop when aerially applied.

A related object of the present invention is to adequately protect the lower plant portions of a corp when the repellent is applied aerially.

An important object of the present invention is to provide a repellent that repels pests from the crops without causing any medical hazard to humans that are often the side effect of chemical pesticides.

Another related object of the present invention is to repel pests that crawl upon the ground to prevent plant injury adjacent the ground.

Yet another basic object of the present invention is to provide a repellent that does not adversely affect the crop upon which it is applied.

A more basic object is to provide a repellent that effectively repels a wide variety of pests.

These and other objects and advantages of the present invention, along with features of novelty appurtenant thereto, will appear, or become apparent, in the course of the following descriptive sections.

DETAILED DESCRIPTION OF A PREFERRED EMBODIMENT

The repellent uses accepted all natural components so that the crops can be grown organically. The repellent comprises a combination of red pepper, powdered garlic and black pepper to repel undesirable pests. Hydrated calcium hydroxide is added to the combination of peppers and garlic to increase the stability of the resultant mixture and provide other beneficial effects.

The repellent comprises, by weight percentage, between 10.7% and 20% red pepper, between 10.7% and 20% powdered garlic, between 10.6% and 20% black pepper, and between 40% and 68% hydrated calcium hydroxide. A particularly potent mixture comprises 10.7% red pepper, 10.7% powdered garlic, 10.6% black pepper, and 68% hydrated calcium hydroxide.

It has been discovered that as an alternative to the exclusive use of calcium hydroxide, an admixture of calcium hydroxide and granulated sulfur, in equal proportions, has been determined to be very beneficial.

The repellent is formulated by combining and mixing the components thoroughly in a mixing chamber. Each component is first ground to a uniform size, preferably at least to about 25 grains. Each component is then added to a conventional mixing apparatus, such as a large tank of the kind commonly found at agricultural cooperatives and normally used to mix fertilizers, or a cement mixer, or the like. Preferably, and as a matter of economy of labor, a preferred mixing tank has a volume of at least 10 cubic yards.

Then the components are blended completely, generally by agitation in a rotating the tank for at least five minutes to produce a homogeneous mixture. It is quite stable and it has a long shelf life. The mixtures may be applied to a selected field in a conventional manner to prevent most pest infestations. For example, the mixture may be applied with tractor mounted dusters or crop dusters, or the like. Tractor mounted dusters, or smaller hand held dusters, would be suitable for smaller tracts of land, while a crop duster would be more efficient for applying the repellent to larger tracts of land. The repellent may be applied in various strengths of between 14 lbs./acre to 30 lbs./acre, but the preferred rate for most applications is 20 lbs./acre. Of course, the repellent can be reapplied as necessary.

After application, the dust coats the bodies and/or breathing apparatus of most pests, including mealy bugs, mites, birds, leaf hoppers, grape leaf skeletonizer, aphids, white flies, other worms, locusts, weevils, etc., that plague many crops, including apples, grapes, almonds, citrus, tomatoes, pecans, melons, etc. The resultant irritating and/or eradicating effect drives the pests from the crops without damaging the crops. The repellent has a long residual lifetime, basically lasting until it is washed away. Of course, the repellent can then be reapplied to regain pest control as necessary.

An ancillary effect of the repellent is its hydrating ability. The calcium hydroxide acts as a desiccant to stop and/or dry up molds and/or fungus. Thus, the farmer may also apply the repellent to the crop to protect it from these as well. Another ancillary effect of the repellent is to function as a fertilizer.

Over time, the calcium hydroxide in the repellent may act as a fertilizer on some soils by increasing soil pH. Of course, the required rate of application is necessarily high to achieve this effect, on the magnitude of one ton of repellent per acre per year. Also, since the peppers contain alkaloids, which are chiefly cyclic nitrogen compounds, over time, they decompose in beneficial nitrogen fertilizer.

From the foregoing, it will be seen that this invention is one well adapted to obtain all the ends and objects herein set forth, together with other advantages which are inherent to the structure.

It will be understood that certain features and subcombinations are of utility and may be employed without reference to other features and subcombinations. This is contemplated by, and is within the scope of, the claims.

As many possible embodiments may be made of the invention without departing from the scope thereof, it is to be understood that all matter herein set forth is to be interpreted as illustrative and not in a limiting sense.

What is claimed is:

1. A pest repellent mixture for application on crops intended to qualify as organically grown, said mixture being adapted to be aerially applied, said mixture consisting of, by weight:

10.7% to 20% red pepper;

10.7% to 20% powdered garlic;

10.6% to 20% black pepper; and,

40% to 68% calcium hydroxide.

2. The repellent as defined in claim 1, wherein said repellent consists essentially of, by weight:

10.7% red pepper;

10.7% powdered garlic;

10.6% black pepper; and,

68% calcium hydroxide.

3. The repellent as defined in claim 1, wherein said repellent consists essentially of, by weight:

20% red pepper;

20% powdered garlic;

20% black pepper; and,

40% calcium hydroxide.

4. A pest repellent mixture for application on crops intended to qualify as organically grown, said mixture being adapted to be aerially applied, said mixture consisting of, by weight:

10.7% red pepper;

10.7% powdered garlic;

10.6% black pepper; and,

34% calcium hydroxide

34% sulfur.

5. A method of repelling pests from organically grown crops, said method comprising the steps of:

(a) combining, by weight, in an essentially homogenius particulate mixture: 20% each of ground red pepper, powdered garlic, particulate black pepper, calcium hydroxide and sulfur to form an essentially homogeneous granular mixture; and, (b) applying the mixture from step (a) to said crops to be protected.

6. The method as described in claim 5, wherein said mixture is aerially applied to said crops.

7. The method as described in claim 1, wherein said red pepper and garlic each comprises 10.7% of said mixture; and black pepper comprises 10.6% and calcium hydroxide comprises 68% thereof.

8. The method as described in claim 7, wherein said calcium hydroxide is replaced by a mixture of calcium hydroxide and sulfur in equal parts.

9. The method as described in claim 7, wherein said mixture is aerially applied to said crops.

10. The repellent as defined in claim 1, wherein the quantity of said calcium hydroxide in said mixture is replaced by equal parts of calcium hydroxide and sulfur.

11. The method as described in claim 10, wherein 40% to 68% of a particulate mixture of equal parts of hydrated calcium hydroxide and sulfur is used to form a granular mixture.

12. A pest repellent mixture for application on crops intended to qualify as organically grown, consisting essentialy of, by weight:

20% red pepper;

20% powdered garlic;

20% black pepper; and,

40% of a particulate mixture of equal parts of hydrated calcium hydroxide and sulfur.

* * * * *